United States Patent [19]
Young

[11] Patent Number: 6,132,435
[45] Date of Patent: Oct. 17, 2000

[54] TORQUE LIMITING DEVICE FOR SURGICAL USE

[75] Inventor: Robert A. Young, West Chester, Pa.

[73] Assignee: Synthes (USA), Paoli, Pa.

[21] Appl. No.: 09/395,151

[22] Filed: Sep. 14, 1999

[51] Int. Cl.[7] .................................................. A61B 17/88
[52] U.S. Cl. ........................ 606/104; 192/56.54; 464/36
[58] Field of Search ................................... 606/103, 104, 606/96, 98, 84, 99, 169, 179; 192/18 R, 134, 56.54, 56.57, 56.62; 464/36, 23

[56] References Cited

U.S. PATENT DOCUMENTS

| | | | |
|---|---|---|---|
| 1,657,274 | 1/1928 | Niedhammer | 192/56.54 |
| 2,344,673 | 3/1944 | Brown | 64/29 |
| 2,576,069 | 11/1951 | Hoag | 64/29 |
| 3,167,936 | 2/1965 | Engquist | 64/29 |
| 3,203,523 | 8/1965 | Gilder et al. | 192/56.54 |
| 3,277,670 | 10/1966 | Bent | 64/29 |
| 3,277,671 | 10/1966 | Winstone | 64/30 |
| 3,305,058 | 2/1967 | Orwin | 192/64 |
| 3,491,839 | 1/1970 | McIntire | 173/93.6 |
| 3,552,147 | 1/1971 | Johansson | 64/29 |
| 3,613,751 | 10/1971 | Juhasz | 144/32 |
| 3,653,226 | 4/1972 | Westbury | 64/29 |
| 3,662,628 | 5/1972 | Schnepel | 81/52.4 |
| 3,667,250 | 6/1972 | Schnepel | 64/29 |
| 3,702,546 | 11/1972 | Schnepel | 64/29 |
| 3,727,432 | 4/1973 | Eaves | 64/29 |
| 3,942,337 | 3/1976 | Leonard | 64/29 |
| 4,007,818 | 2/1977 | Orwin | 192/56 |
| 4,041,729 | 8/1977 | Bilz | 62/29 |
| 4,174,621 | 11/1979 | Woltjen | 64/29 |
| 4,262,501 | 4/1981 | Vaughn | 64/29 |
| 4,668,206 | 5/1987 | Fukumoto | 464/36 |
| 4,712,456 | 12/1987 | Yuan | 81/473 |
| 4,867,019 | 9/1989 | Lankry | 81/474 |
| 4,880,064 | 11/1989 | Willoughby | 173/12 |
| 4,991,701 | 2/1991 | Nakano | 192/56 |
| 5,004,054 | 4/1991 | Sheen | 173/12 |
| 5,035,311 | 7/1991 | Girguis | 192/56 |
| 5,054,588 | 10/1991 | Thorp | 192/0.034 |
| 5,156,244 | 10/1992 | Pyles | 192/0.034 |
| 5,310,010 | 5/1994 | Lo | 173/178 |
| 5,356,350 | 10/1994 | Schreiber | 475/153 |
| 5,383,818 | 1/1995 | Lessat-Kaupat | 464/36 |
| 5,437,524 | 8/1995 | Huang | 408/139 |
| 5,505,676 | 4/1996 | Bookshar | 477/178 |
| 5,569,118 | 10/1996 | Holmin | 477/178 |
| 5,855,517 | 1/1999 | Lepold | 464/36 |
| 5,868,231 | 2/1999 | Kampf | 192/56.62 |
| 5,888,200 | 3/1999 | Walen | 606/167 |

FOREIGN PATENT DOCUMENTS

| | | |
|---|---|---|
| 1 329 877 | 9/1973 | United Kingdom . |
| 1 415 138 | 11/1975 | United Kingdom . |

*Primary Examiner*—Pedro Philogene
*Attorney, Agent, or Firm*—Pennie & Edmonds LLP

[57] ABSTRACT

The present invention is directed to a device for limiting the maximum torque that is applied to a screw during a surgical procedure. The driving connection between the input and output shafts of the device is established through a plurality of transmission balls, which are maintained in position by the action of an elastic element within the torque limiting device. When the counter-torque created by the resistance of the screw exceeds the torque exerted by the elastic element, the transmission balls are caused to be disengaged, thereby severing the driving connection between the input and output shafts and preventing overtightening of the screw. The present torque limiter can be fully sterilized by autoclaving, as required for use in a surgical setting.

8 Claims, 5 Drawing Sheets

TORQUE LIMITING DEVICE FOR SURGICAL USE

FIELD OF INVENTION

The present invention relates to a device for adjusting and limiting the amount of torque applied to a bone screw during power insertion.

BACKGROUND OF THE INVENTION

Locking screws, or bone screws, are commonly used during surgery to aid in the proper setting of bone fractures, e.g., to lock a plate to the bone across the area of the fracture in order to align and stabilize the bone fragments and to transfer the load from the bone to the plate. Bone screws are typically self-drilling and self-tapping and therefore require insertion by a drill or other power device, which typically rotate at speeds of the order of 1,000 RPM. If all the torque of the drill were continuously transmitted to the screw head, however, the screw would strip once it meets a certain resistance. As a result, a device is needed for use in a surgical setting to limit the amount of torque that is applied to the screw head.

Torque limiting devices have been developed for other applications to limit the amount of torque applied by a power tool to a workpiece. Examples of prior art devices include those disclosed in U.S. Pat. Nos. 5,437,524, 5,004,054, 4,867,019, 4,712,456, and 4,262,501. None of these devices, however, was designed for use in a surgical setting. Tests performed on certain of these prior art de rices show that they cannot be autoclaved, as required for use in the sterile environment of an operating room. For example, prior art devices typically use heavy greases or oils that cannot be sterilized or that degrade if autoclaved. In addition, prior art devices commonly use a coil spring to establish the drive connection between the drive plates. The elasticity of a coil spring may change, however, with repeated exposure to the high temperatures required for autoclaving, which affects the ability of the operator to set accurately the maximum torque exerted by the torque limiter. Also, prior art devices accumulate internally dust, grit, or rust as a result of abrasion of their moving parts, which in turn affects the ability to autoclave the device.

As the above discussion illustrates, there is a need for a torque limiting device that can be used in a surgical setting.

SUMMARY OF THE INVENTION

The present invention relates to a torque limiting device for use in a surgical setting. In the preferred embodiment, the torque limiting device comprises: (a) a base unit; (b) a housing; (c) an output shaft, about which is mounted a flange; (d) a drive connection; and (e) an elastic element. The base unit, which is preferably screwed into the housing, serves to transmit the rotational energy from the power drill into the drive connection of the device. The drive connection comprises a plurality of transmission balls engaged between divots in the inner surface of the base unit and complementary recesses in the opposing surface of the flange, which is mounted on the output shaft that is operatively connected to the screw-driving bit. The transmission balls are maintained in the divots by the force of a plurality of spring washers, which acts between the flange on the output shaft and the end of the housing opposite the base unit. As the screw tightens in the bone, it will exert a torque on the transmission balls, such torque being transmitted through the output shaft and the flange in which the balls are engaged. The torque generated by the screw is opposite to that generated by the force of the elastic element. Once the counter-torque generated by the screw exceeds the torque generated by the force of the elastic element, the counter-torque will force the balls from the divots in the base unit, thereby levering the drive connection between the base unit and the output shaft and preventing the screw from being overtightened. The maximum torque applied to the screw can be adjusted by screwing the base unit into or out of the housing, thereby compressing or relaxing the elastic element and accordingly increasing or decreasing the force—and hence the torque—exerted by the elastic element on the transmission balls.

The torque limiting device is designed to sustain the high revolutions (of the order of 1,000 RPM) and sterilization procedures required for use in a surgical setting. In the preferred embodiment, the divots in the base unit are shaped in such a manner as to ease the rolling action of the transmission balls into and out of such divots, thereby reducing the abrasion of the moving parts and hence the amount of dirt, grit, or rust that may accumulate as a result of repeated use and autoclaving. This feature also eliminates the need for heavy lubricating oils or greases, which cannot be sterilized or which degrade under high temperatures. The preferred embodiment also uses a plurality of spring washers, instead of a coil spring, as the elastic element. The elasticity of the spring washers changes very little after initial exposure to the high temperatures required for autoclaving. Although a coil spring or other elastic element might be used in the alternative, the elasticity of a coil spring may continually change with repeated autoclaving, thereby impeding the ability to adjust accurately the maximum torque setting of the device. Accurate adjustment of the device over a wide range of torque settings is also made possible by the feature of screwing the base unit into and out of the housing.

Other features of the invention are set forth below.

BRIEF DESCRIPTION OF DRAWINGS

Preferred features of the present invention are disclosed in the accompanying drawings, wherein similar reference character, denote similar elements throughout the several views, and wherein.

DETAILED DESCRIPTION OF THE PREFERRED EMBODIMENTS

Figure 1:
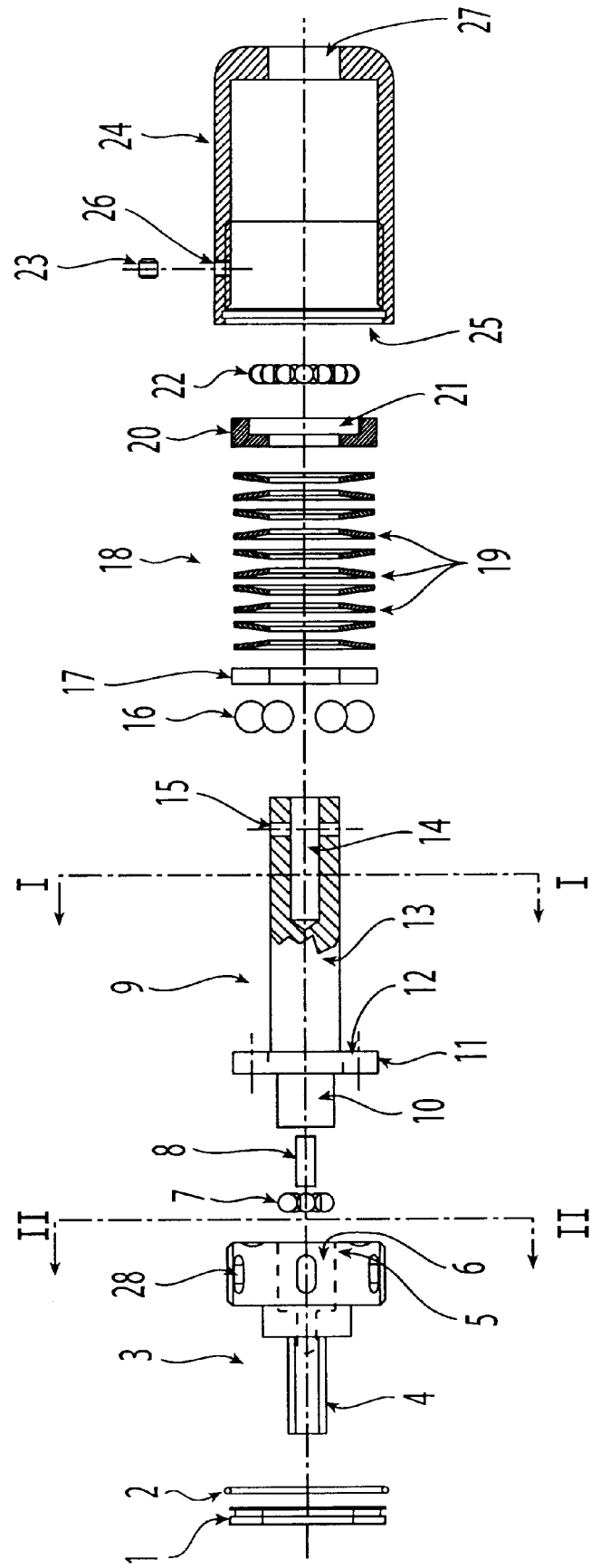
FIG. 1 shows an exploded view of an embodiment of the torque limiting device.
Figure 2:
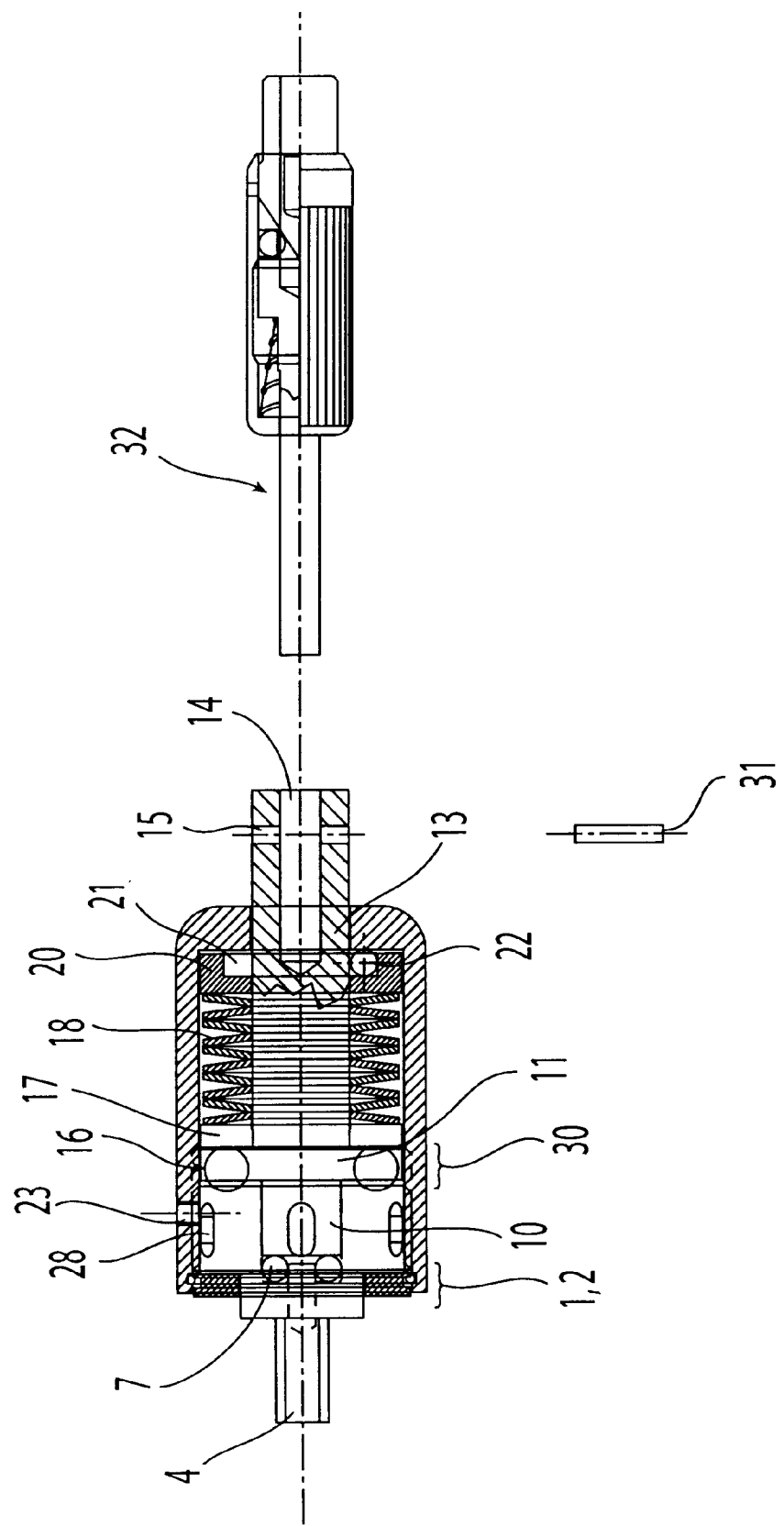
FIG. 2 shows an assembled sectional side view of the present invention according to FIG. 1.
Figure 3:
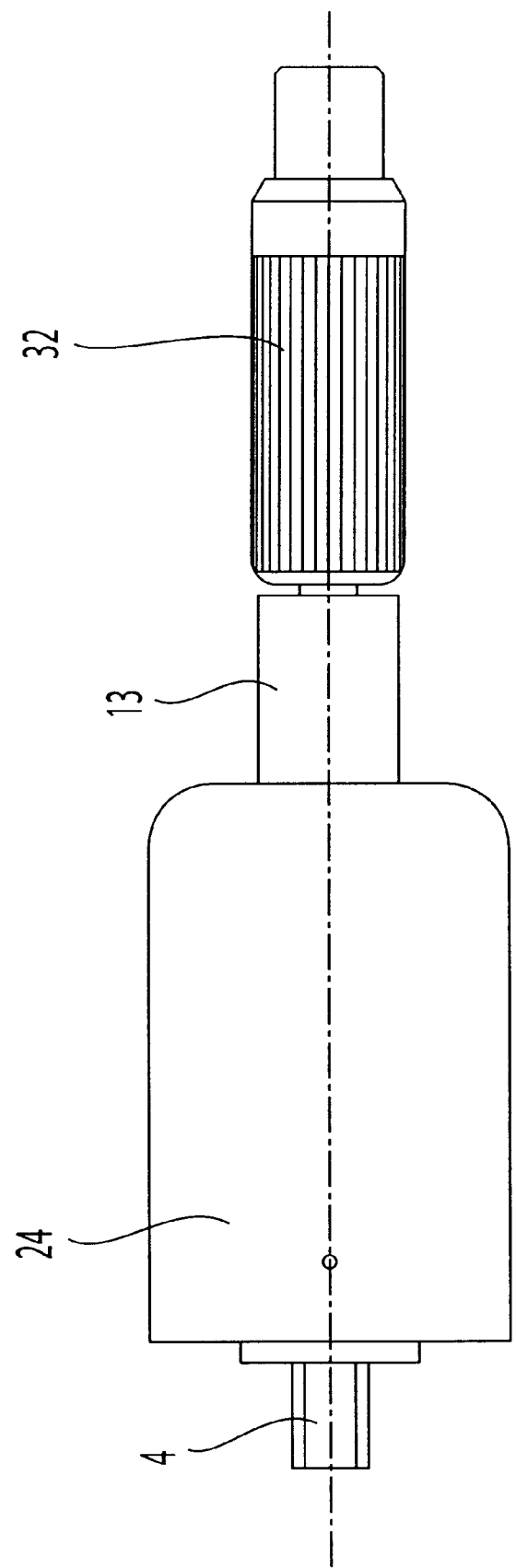
FIG. 3 shows an external view of the assembled invention according to FIG. 2.
Figure 4:
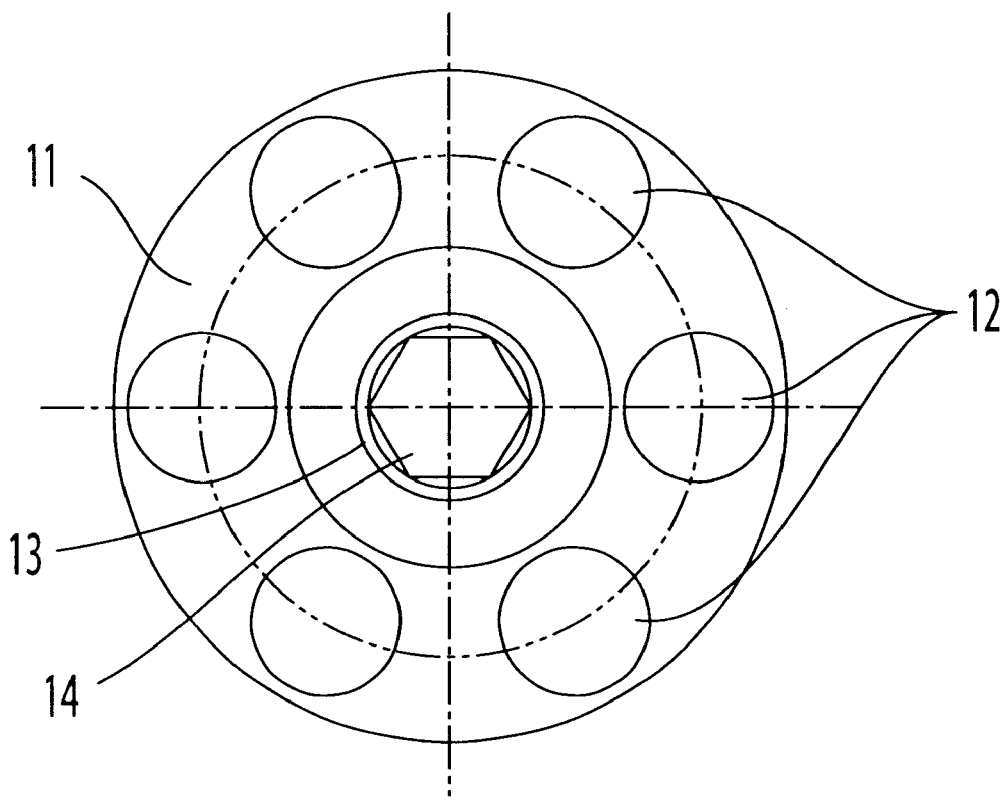
FIG. 4 is a cross-sectional view of the input shaft and flange on line I—I of FIG. 1, with the housing and transmission balls removed.

Referring to FIGS. 1–5, the preferred embodiment of the present invention comprises five main components:

(a) the base unit 3, which is formed of one piece comprising input stem 4 and hub 5;

(b) the shaft 9, comprising the interior shaft portion 10, flange 11, and output shaft portion 13;

(c) the external housing 24;

(d) a drive connection 30, comprising transmission balls 16 occupying divots 29 in hub 5 and through holes 12 in flange 11; and (e) an elastic element 18, comprising a plurality of spring washers 19.

The invention is assembled in the following manner:

Base unit 3 is constructed of a single unit comprising the input stem 4 and the hub 5. The input stem 4 is designed such that it may be secured in the chuck of a drill, rotary tool, or other such instrument. The outer surface of the hub 5 is threaded (not shown) so that it may be screwed into the large threaded opening 25 at one end of the housing 24. The set screw 23 is screwed into the small threaded opening 26 in the surface of the housing 24 to engage one of the grooves 28 in the side of hut 5, thereby preventing the base unit 3 from turning relative to the housing 24. The base unit 3 is further secured in place by means of the snap ring 2 and the rear housing plate 1. The base unit 3 and housing 24 will therefore rotate as a single unit, either with or about the shaft 9, in the manner described in a later paragraph.

The shaft 9, partially located within the housing 24, is constructed of a single piece comprising the small interior shaft portion 10, the flange 11, and the output shaft portion 13. The interior shaft portion 10 rotates within the recess 6 in the hub 5. The ball bearings 7 and dowel pin 8 also fit in the recess 6 to facilitate rotation of the interior shaft portion 10. The interior shaft portion 10 is joined to the flange 11, which is joined to the output shaft portion 13, which extends from the flange 11 through the small opening 27 in the housing 24 opposite the large threaded opening 25. At the end of the output shaft portion 13 is an opening 14, in which is inserted a standard coupling device 32 for holding the drill bit, screwdriver bit, or like object (not shown). The coupling device 32 is secured in the opening 14 by means of a dowel pin 31, which passes through the hole 15 in the output shaft portion 13 and a hole (not shown) in the coupling device 32. The input stem 4, hub 5, interior shaft portion 10, flange 11, output shalt portion 13, housing 24, and the coupling device 32 all share a common axis of rotation.

The drive connection 30 between the hub 5 and the output shaft portion 10 is established by means of a plurality of transmission balls 16. In the preferred embodiment, the transmission balls 16 are located in the through holes 12 of the flange 11, said through holes 12 being shown in FIG. 4. The transmission balls 16 are maintained in the through holes 12 by the flat bearing washer 17, which is disposed about the output shaft 13 to cover the face of the flange 11 opposite the hub 5. The surface of the flat bearing washer 17 is hardened to reduce wear and abrasion, thereby reducing the amount of dust, grit or rust that may accumulate in the device. In the alternative the transmission balls 16 could be located in recesses (not shown), rather than through holes, in the surface of the flange 11, although this would require the more complicated process of hardening the surface of the flange 11 instead of the separate flat bearing washer 17. The use of through holes instead of recesses in the flange 11 offers the additional advantage what there is no axial motion of the shaft 9 and correspondingly no hammering or impact on the drill bit or screw. In either embodiment, the diameter of each transmission tall 16 is somewhat larger than the depth of the through hole 12 or recess in flange 11, such that a small portion of each transmission ball 16 extends beyond the flange 11 to engage the divots 29 in the inner surface of the hub 5. The number and placement of the divots 29 correspond to the number and placement of the through holes 12 in flange 11, such that each transmission ball 16 can simultaneously engage both a divot 29 and a through hole 12.

The drive connection 30 between the base unit 3 and shaft 9 is maintained by means of an elastic element 18, which in the preferred embodiment comprises a plurality of spring washers 19. Spring washers 19 are preferred because their elasticity will not be affected by the high temperatures required for repeated autoclaving, although a coil spring or other elastic element might be used as well. The spring washers 19 exert a force against the flat bearing washer 17 at one end and the thrust bearing washer 20 at the other end. The thrust bearing washer 20 has an opening 21, through, which passes the output shaft portion 13. A plurality of ball bearings 22 is disposed about the output shaft portion 13 in the opening 21 in order to facilitate the rotation of the output shaft portion 13 in the housing 24.

Figure 5:
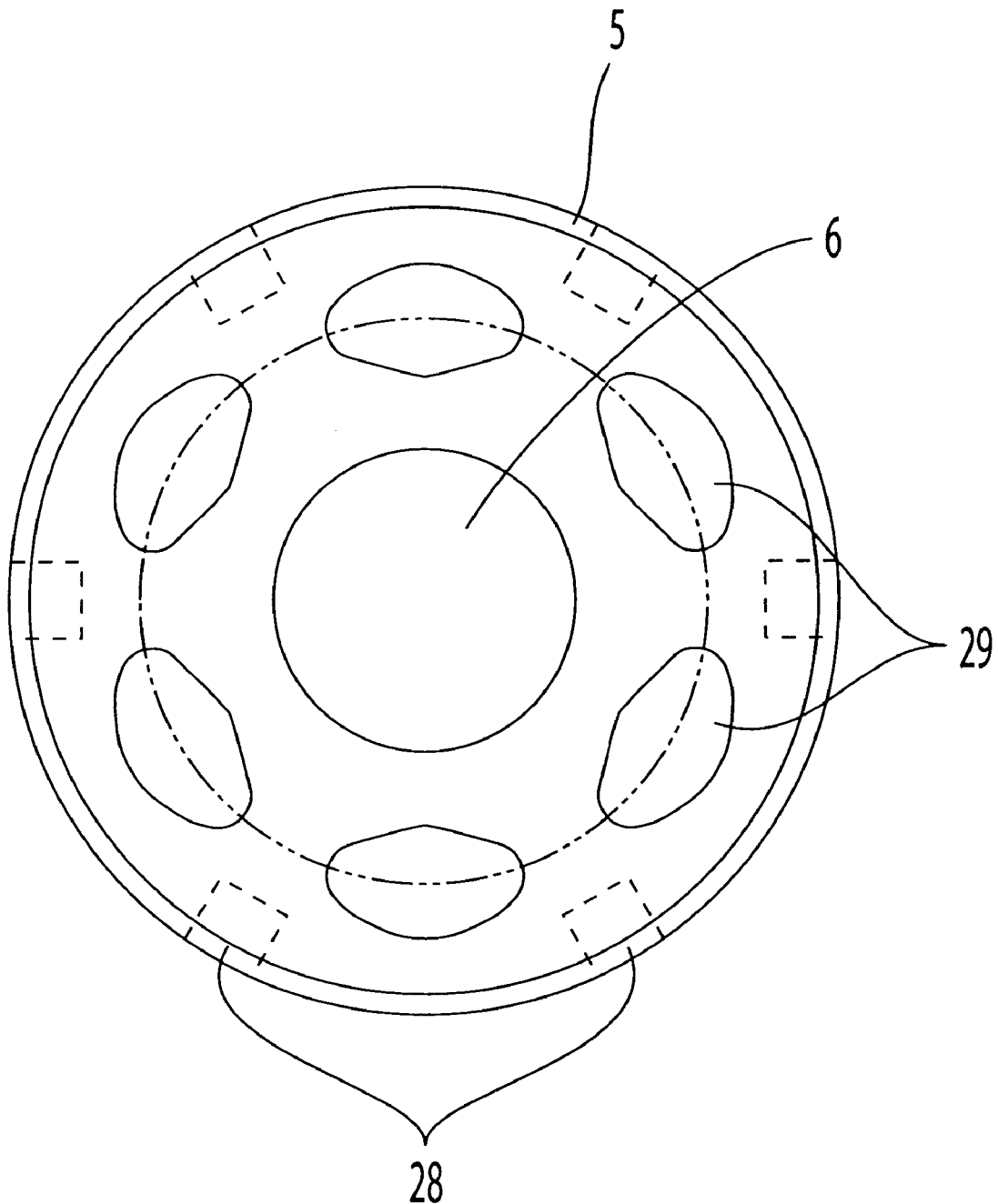
FIG. 5 is a cross-sectional view of the inner surface of the base unit on line II—II of FIG. 1, with the output shaft, transmission balls, and housing removed.

The force of the spring washers 19 against the flat bearing washer 17 maintains the transmission balls 16 in the divots 29 in the hub 5, thereby establishing a drive connection between the base unit 3 and the shaft 9. Rotation of the stem 4 by a rotary or other device thereby results in rotation of the drill bit in out put shaft 13. As the screw (not shown) tightens in the bone, the screw will exert a counter-torque on the output shaft portion 13, which will be transmitted to the transmission balls 16 by flange 11. Once the counter-torque on the transmission balls 16 exceeds the torque from spring washers 19, the counter-torque will cause the transmission balls 16 to disengage from the divots 29, thus severing the drive connection 30 between the input stem 4 and the shaft 9 and thereby preventing overtightening of the screw. In the preferred embodiment, the divots 29, shown in FIG. 5, are shaped by using a ball end mill to form the indentations as the base unit 3 is rotated about its axis. The resultant shape of the divots 29, which might be called a "curved ellipse," eases the rolling action of the transmission balls 16 into and out of such divots 29, thereby reducing the abrasion of the moving parts and hence the amount of dirt, grit, or rust that may accumulate as a result of repeated use and autoclaving. This shape also eliminates the need for heavy lubricating oils or greases, which cannot be sterilized or which degrade with autoclaving. The curved ellipse shape is also symmetrical, in that the transmission balls 16 encounter the same shape regardless of whether the transmission balls 16 are moving about the axis of rotation of the device in a clockwise or counterclockwise direction. This symmetrical feature permits the device to be used for either right-handed or left-handed screws, or for either the insertion or removal of such screws.

The maximum torque that may be exerted on the screw is a function of the force exerted by the spring washers 19 against the transmission balls 16. Thus, the maximum torque exerted on the screw can be adjusted by increasing or decreasing the force exerted by the spring washers 19, which can be accomplished by decreasing or increasing the effective length occupied by the spring washers 19 within the housing 24. In the preferred embodiment, the length occupied by the spring washers 19, and thus the maximum torque exerted on the screw, is adjusted by loosening the set screw 23; screwing base unit 3 into or out of the housing 24 until the desired torque setting is reached; and then retightening the set screw 23 to engage one of the grooves 28 in the hub 5 to secure the base unit 3 in the housing 24. The screwing feature of base unit 3 and the presence of multiple grooves 28 to engage set screw 23 permit the accurate adjustment of the maximum torque of the invention over a wide range of torque settings.

All of the components of the preferred embodiment described above are constructed of stainless steel or other material that will reduce wear and abrasion, can be sterilized, and can endure repeated autoclaving. Although other materials might be used as well, there may be a resultant degradation in performance, accuracy, or endurance.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A torque-limiting device for surgical use, comprising:

a rotatable housing having first and second ends;

a base unit engaged within the first end of said housing, said base unit having an input stem for engagement with a rotary device;

an output shaft extending through the second end of said housing, said output shaft having a flange disposed about said shaft, said flange and said base unit having adjacent faces;

a plurality of recesses in said faces of said base unit and said flange, said recesses being positionable for mutual alignment;

a ball located in and between each pair of said opposing recesses; and an elastic element disposed about said input shaft between said flange and said second opposing end of said housing, said elastic element exerting a force to maintain a drive connection between said balls and said opposing faces, said drive connection being severed when the torque exerted on said balls by said elastic element is exceeded by the counter-torque exerted on said balls by said flange.

2. The torque-limiting device of claim 1, wherein the base unit is threadably engaged in the first end of said housing, and the torque is adjustable by screwing said base unit into or out of said housing, thereby causing said elastic element to compress or expand.

3. The torque-limiting device of claim 1, wherein said recesses in the face of said flange extend through said flange, and further comprising a disc unit disposed about said shaft unit between said flange and said elastic element to maintain said balls in said recesses in said flange.

4. The torque-limiting device of claim 1, wherein said recesses in the face of said base unit are symmetrical, such that said balls encounter the same shape of said recess regardless of whether said balls are moving about the axis of rotation of said device in a clockwise or counterclockwise direction.

5. The torque-limiting device of claim 1, wherein said recesses in the face of said base unit are formed in the shape of curved ellipses, in which the ends of said curved ellipses lie on a circle formed by the rotation of said base unit about its axis, to facilitate the rolling action of said balls into and out of said recesses in said base unit.

6. The torque-limiting device of claim 1, wherein the elastic element comprises a plurality of spring washers.

7. A torque-limiting device according to claim 1, wherein said housing, said base unit, said input stem, said output shaft, said flange, said balls, said disc unit, and said elastic element are constructed of stainless steel.

8. A torque-limiting device according to claim 1, wherein all components of said device can be sterilized by autoclaving without affecting the operation of the device.

* * * * *